United States Patent [19]

Malfroot et al.

[11] Patent Number: 4,697,032
[45] Date of Patent: Sep. 29, 1987

[54] PROCESS FOR THE PREPARATION OF 1-BROMOETHYL HYDROCARBONYL CARBONATES AND NEW 1-BROMOETHYL HYDROCARBONYL CARBONATES

[75] Inventors: Thierry Malfroot, Saintry sur Seine; Marc Piteau, Itteville; Jean-Pierre Senet, La Chapelle la Reine, all of France

[73] Assignee: Societe Nationale des Poudres et Explosifs, Paris, France

[21] Appl. No.: 796,555

[22] Filed: Nov. 8, 1985

[30] Foreign Application Priority Data

Nov. 23, 1984 [FR] France ................................ 84 17847

[51] Int. Cl.$^4$ ............................................. C07C 68/06
[52] U.S. Cl. .................................... 558/270; 558/260; 558/277
[58] Field of Search ...................... 558/260, 270, 277

[56] References Cited

PUBLICATIONS

Vaya et al, Chem. Abs., vol. 101:130508m.
Astra, Chem. Abs., vol. 101:23218v.

*Primary Examiner*—Michael L. Shippen
*Attorney, Agent, or Firm*—Bucknam and Archer

[57] ABSTRACT

The invention relates to a process for the preparation of 1-bromoethyl hydrocarbonyl carbonates, characterized in that anhydrous hydrobromic acid is reacted with a vinyl hydrocarbonyl carbonate of formula

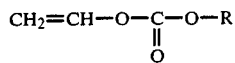

in which R denotes a saturated, substituted or unsubstituted $C_1$–$C_{12}$ aliphatic radical or $C_5$–$C_{24}$ alicyclic radical, or a substituted or unsubstituted aromatic radical, at a temperature between 10° and 100° C.

The invention also relates to the new 1-bromoethyl hydrocarbonyl carbonates of formula:

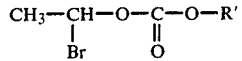

These carbonates are particularly sought after for introducing a carbonate group into a molecule.

6 Claims, No Drawings

PROCESS FOR THE PREPARATION OF 1-BROMOETHYL HYDROCARBONYL CARBONATES AND NEW 1-BROMOETHYL HYDROCARBONYL CARBONATES

The invention relates to a new process for the preparation of 1-bromoethyl hydrocarbonyl carbonates. The invention also relates to new 1-bromoethyl hydrocarbonyl carbonates. While some alpha-bromo carbonates are mentioned in a small number of publications, only 1-bromoethyl ethyl carbonate appears to have been the subject of an accurate description. Its preparation does not appear to be easy. Various preparative processes have been suggested. One of these consists in reacting a 1-bormoethyl haloformate with ethanol, according to the reaction:

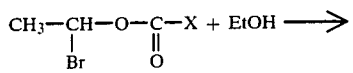

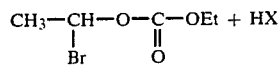

where X denotes chlorine or bromine.

The difficulty of this process lies in producing the starting bromo haloformate

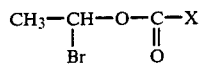

According to European Patent Application EP No. 108,547, a radical bromination of ethyl chloroformate or of ethyl bromoformate is carried out.

This radical bromination has disadvantages: the UV lamps which are employed in preference to free-radical initiators consume large amounts of energy, all the more so since the reaction times are long when this method is used. Various brominated byproducts are always produced.

It is also possible to prepare 1-bromoethyl bromoformate by the reaction of acetaldehyde with bromophosgene, as described in French Patent Application FR No. 2,532,933. However, catalysts must then be used, and bromophosgene is not a commercially available reactant. It is relatively unstable and very difficult to prepare. It is manufactured, for example, by the reaction of carbon monoxide with bromine, but this reaction requires highly specialized industrial equipment.

Another process for the preparation of 1-bromoethyl ethyl carbonate consists in brominating diethyl carbonate using a radical process. The same disadvantages are encountered again as in the radical methods described earlier: formation of byproducts and large energy requirements. In addition, this process is unsuitable for the preparation of some other 1-bromoethyl carbonates because in some compounds the bromine will attach itself to the other hydrocarbon group in a greater quantity; for example, when attempts are made to bond bromine to ethyl isopropyl carbonate, 1-bromoisopropyl ethyl carbonate is predominantly obtained.

It is also possible to use 1-chloroethyl ethyl carbonate as a starting material and to effect a substitution of chlorine by bromine by means of an organic salt, as indicated in the application EP No. 108,547. This method also has disadvantages, because the substitution reaction is slow and imcomplete.

For example, a mixture consisting of only 65% of 1-bromoethyl ethyl carbonate and 35% of 1-chloroethyl ethyl carbonate is obtained (Example 12 of the above-mentioned application) and the separation of the α-chlorocarbonate from the α-bromocarbonate is very difficult, as for all the other lower alkyl carbonates.

It has long been known that the carbon-bromine bond is much easier to break than the carbon-chlorine bond. α-Bromo carbonates are consequently especially sought after, for example, for the introduction of carbonate groups into a molecule. The ability to produce most of them easily and in good yields is consequently of great interest. It is found, however, that the above processes are not wholly satisfactory.

A new process for the preparation of 1-bromoethyl hydrocarbonyl carbonates has now been found.

According to this process, anhydrous hydrobromic acid is reacted with a vinyl hydrocarbonyl carbonate of formula

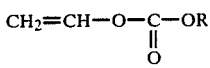

in which R denotes a saturated, substituted or unsubstituted $C_1$-$C_{12}$ aliphatic radical or $C_5$-$C_{24}$ alicyclic radical, or a substituted or unsubstituted aromatic radical, at a temperature between 10° and 100° C.

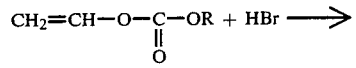

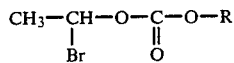

The addition of hydrobromic acid to various unsaturated compounds has been the subject of different investigations (see Houben-Weyl "Methoden der organischen Chemie" vol. 5/4 pp. 107–127). The addition of this acid to an unsaturated bond adjoining a carbonate group has never been envisaged until now. While it is relatively easy in the case of simple olefinic compounds, the presence of functional groups on the carbon bearing the double bond makes the reaction outcome quite unpredictable. Thus, for example, hydrobromic acid immediately decomposes vinyl ethyl ether

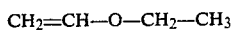

and no formation of the bromo derivative is observed. The same might be expected to happen during the fixation of the acid to an unsaturated bond adjacent to an oxygen forming part of a carbonate group. However, surprisingly, means have now been found for effecting the addition of hydrobromic acid to vinyl carbonates, the addition being moreover selective, the bromine being fixed solely in the alpha position.

The vinyl hydrocarbonyl carbonates employed as starting materials may be obtained according to conventional methods, for example by condensation of vinyl chloroformate with alcohols or phenols, as indicated in U.S. Pat. Nos. 2,377,111, 2,384,143 and 3,905,981, or by the pyrolysis of carbonates according to the process described in U.S. Pat. No. 2,370,549.

The substituent or the substituents in R are generally chosen from the group comprising halogen atoms and radicals not bearing functions with which hydrobromic acid is liable to react. Among the latter, saturated hydrocarbon radicals are suitable.

The hydrobromic acid must be anhydrous. A slight excess is generally used, for example of the order of 1.05 to 1.4 equivalents per equivalent of vinyl carbonate to be treated.

According to a preferred version of the invention, gaseous hydrobromic acid is introduced slowly into the reaction medium.

The reaction is carried out in the absence of solvent.

The preferred temperature is between 15° and 60° C. In general, the reaction takes only a few hours. The carbonates are then recovered using conventional methods, generally by distillation under reduced pressure.

The process according to the invention is simple. Its use requires neither costly equipment nor a large expenditure of energy. It enables 1-bromoethyl hydrocarbonyl carbonates to be obtained in a high purity, in contrast to the chlorine-bromine exchange process, in which contamination by α-chlorocarbonates occurs and in the radical bromination process, in which many other brominated products are obtained.

The invention also relates to the new 1-bromoethyl hydrocarbonyl carbonates of formula

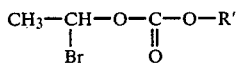

in which R' is a saturated, substituted or unsubstituted $C_1$ or $C_3$-$C_{12}$ aliphatic radical or $C_5$-$C_{24}$ alicyclic radical, or a substituted or unsubstituted aromatic radical.

The substituent or the substituents in R' are generally chosen from the group comprising halogen atoms and radicals not bearing groups liable to react with hydrobromic acid. Among the latter radicals, saturated hydrocarbon radicals are suitable.

The invention relates more particularly to 1-bromoethyl isopropyl, 1-bromoethyl, n-octyl and 1-bromoethyl phenyl carbonates.

1-Bromoethyl hydrocarbonyl carbonates are synthesis intermediates which may, for example, advantageously replace their less reactive chloro homologues or more unstable iodo homologues in many reactions.

One of their important applications is the modification of carboxylic acid groups in various compounds. The reaction can be depicted as follows:

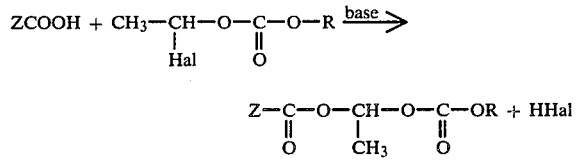

This application is described, in particular, in French Patent Application No. 2,532,933 and European Patent Application No. 108,547.

1-Bromoethyl carbonates can also react with phosphoric acid derivatives, as indicated in German Application No. 2,628,410:

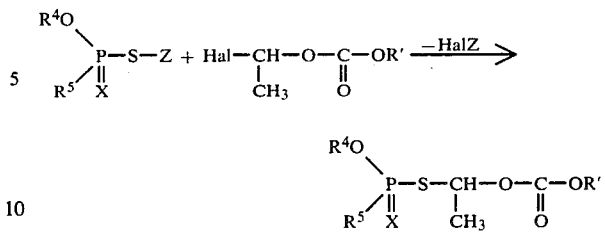

Since the C—Br bond is much more labile than the C—Cl bond, α-bromo carbonates can be employed in a smaller quantity than the corresponding α-chloro carbonates. The reaction conditions are milder and, as a result, some degradation of the starting compound is eliminated. The yields are higher.

Furthermore, α-bromo carbonates are much more stable than the corresponding iodo carbonates; when the former replace the latter it becomes possible to obtain products of higher purity and in greater quantity.

The following examples are given by way of illustration:

EXAMPLE 1

Preparation of 1-bromoethyl ethyl carbonate

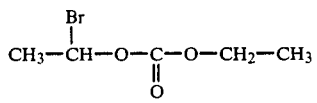

58 g (0.5 mole) of vinyl ethyl carbonate are introduced into a reactor fitted with a stirrer, a thermometer, a reflux condenser and a tube for introducing gas.

A gaseous stream of 48 g of anhydrous hydrobromic acid is passed in over 1 h 15 min, with stirring. The temperature gradually rises from 16° to 35° C.

Excess hydrobromic acid is then removed by degassing with nitrogen for 2 h at 20° C.

The product obtained is purified by distillation under reduced pressure. In this way, 75 g (76% yield) of 1-bromoethyl ethyl carbonate are collected, with the following properties:

Boiling point (B.p.): 66°–68° C./12 mm Hg
$n_D^{20}$: 1.4410
$d_4^{20}$: 1.4265
$^1$H NMR (CCl$_4$, δ ppm): 1.3 (1, 3H); 1.95 (d, 3H); 4.15 (9, 2H); 6.55 (9, 1H);
IRγ(C=O): 1770 cm$^{-1}$

EXAMPLE 2

Preparation of 1-bromoethyl ethyl carbonate

The operation is carried out as in Example 1 but starting with 259 g (2.23 moles) of vinyl ethyl carbonate and 210 g (2.59 moles) of anhydrous gaseous hydrobromic acid. The addition time of hydrobromic acid is 8 h, the temperature changing between 16° and 35° C.

After the reaction mixture has been treated as in Example 1, 378 g of 1-bromoethyl ethyl carbonate are obtained (86% yield).

B.p.: 75° C./15 mm Hg.

EXAMPLE 3

Preparation of 1-bromoethyl n-octyl carbonate

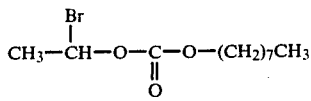

The operation is carried out as in Example 1, starting with 0.5 mole of vinyl n-octyl carbonate and 0.59 mole of anhydrous gaseous hydrobromic acid.

The addition time of hydrobromic acid is 3 h, the temperature being maintained at 25° C.

After distillation under reduced pressure (122° C./4 mm Hg), 1-bromoethyl n-octyl carbonate is obtained in 83% yield.

IR (C=O): 1765 cm$^{-1}$ $^1$H NMR (CCl$_4$, δ ppm): 0.9 (t, 3H); 1.10–1.9 (m, 12H); 2 (d, 3H, J=6 Hz); 4.15 (t, 2H, J=6 Hz); 6.55 (q, 1H, J=6 Hz)

EXAMPLE 4

Preparation of 1-bromoethyl isopropyl carbonate

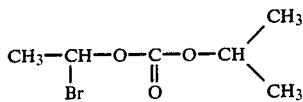

The operation is carried out as in Example 1 with 0.5 mole of vinyl isopropyl carbonate and 0.58 mole of anhydrous gaseous hydrobromic acid.

The addition time of hydrobromic acid is 4 hours, the temperature being maintained at 30° C.

After distillation under reduced pressure (78° C./16 mm Hg), 1-bromoethyl isopropyl carbonate is obtained in 80% yield.

IR γ(C=O): 1760 cm$^{-1}$ $^1$H NMR (CCl$_4$, δ ppm): 1.3 (d, 6H, J=6 Hz); 2 (d, 3H, J=6 Hz); 4.9 (sept, 1H, J=6 Hz); 6.55 (q, 1H, J=6 Hz)

$d_4^{20}$ = 1.3424

$n_D^{20}$ = 1.4372

EXAMPLE 5

Preparation of 1-bromoethyl phenyl carbonate

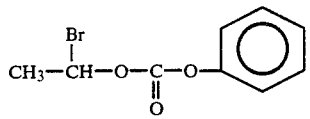

The operation is carried out as in Example 1, with 0.5 mole of vinyl phenyl carbonate and 0.6 mole of anhydrous gaseous hydrobromic acid. Hydrobromic acid is added for 6 h at 20° C. and then 2 h at 50° C.

After distillation under reduced pressure (126° C./5.5 mm Hg), 1-bromoethyl phenyl carbonate is obtained in 80% yield.

IR ν(C=O): 1765 cm$^{-1}$ $^1$H NMR (CCl$_4$, δ ppm): 2 (d, 3H, J=6 Hz); 6.6 (q, 1H, J=6 Hz); 7.2 (m, 5H)

We claim:

1. A process for the preparation of a 1-bromoethyl hydrocarbonyl carbonate, which consists of reacting anhydrous hydrobromic acid with a vinyl hydrocarbonyl carbonate of formula

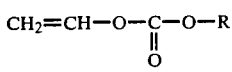

wherein R is a saturated, C$_1$–C$_8$ aliphatic radical or alicyclic radical or an aromatic radical, wherein said aliphatic, alicyclic or aromatic radical is unsubstituted or substituted by halogen atoms or saturated hydrocarbon radicals, at a temperature between 10° C. and 100° C. and isolating said 1-bromoethyl hydrocarbonyl carbonate from the reaction mixture.

2. The process for the preparation of a 1-bromoethyl hydrocarbonyl carbonate of formula

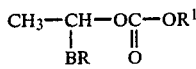

wherein R$^1$ is ethyl, isopropyl, n-octyl or phenyl, which consists of reacting anhydrous hydrobromic acid with a vinyl hydrocarbonyl carbonate of formula

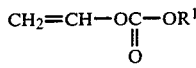

wherein R$^1$ is as defined hereinabove at a temperature between 10° C. and 100° C. and isolating said 1-bromoethyl hydrocarbonyl carbonate from the reaction mixture.

3. The process according to claim 1, wherein gaseous hydrobromic acid is slowly introduced into the reaction medium.

4. The process according to claim 1, wherein hydrobromic acid is added in a quantity of between 1.05 and 1.4 equivalents per equivalent of vinyl carbonate.

5. The process according to claim 1, wherein the reaction is carried out in the absence of solvent.

6. The process according to claim 5, wherein the reaction temperature is between 15° and 60° C.

* * * * *